US010322197B1

(12) United States Patent
Williams

(10) Patent No.: US 10,322,197 B1
(45) Date of Patent: Jun. 18, 2019

(54) SELF-CLEANING RETRACTABLE PARTITION APPARATUS

(71) Applicant: Isaiah Maurice Williams, Parrish, FL (US)

(72) Inventor: Isaiah Maurice Williams, Parrish, FL (US)

( * ) Notice: Subject to any disclaimer, the term of this patent is extended or adjusted under 35 U.S.C. 154(b) by 0 days.

(21) Appl. No.: 16/209,225

(22) Filed: Dec. 4, 2018

(51) Int. Cl.
 *A61L 2/10* (2006.01)
 *A47G 5/02* (2006.01)
 *E06B 9/24* (2006.01)
(52) U.S. Cl.
 CPC .................. *A61L 2/10* (2013.01); *A47G 5/02* (2013.01); *E06B 9/24* (2013.01); *A61L 2202/25* (2013.01)
(58) Field of Classification Search
 CPC ......... A61L 2/10; A61L 2202/25; A47G 5/02; E06B 9/24
 See application file for complete search history.

(56) References Cited

U.S. PATENT DOCUMENTS

| 4,825,921 A | 5/1989 | Rigter |
| 8,881,787 B2 | 11/2014 | Wang |
| 2007/0193705 A1 | 8/2007 | Hsu |
| 2015/0152683 A1* | 6/2015 | Lu .............................. E06B 9/56 160/323.1 |
| 2017/0325605 A1 | 11/2017 | Korn |
| 2018/0289847 A1* | 10/2018 | McCormick .............. A61L 2/26 |

FOREIGN PATENT DOCUMENTS

| EP | 1 366 698 A1 | 10/2002 |
| WO | WO 2010/109247 A2 | 3/2010 |

* cited by examiner

*Primary Examiner* — Sean E Conley
(74) *Attorney, Agent, or Firm* — Dale J. Ream

(57) ABSTRACT

A self-cleaning retractable partition apparatus includes a tower assembly defining an interior area, and a primary ultraviolet light mounted to bottom and top walls thereof operable to illuminate the interior area. A partition assembly in the tower assembly includes a reel and a flexible panel movable between coiled and uncoiled configurations wrapped about the reel. A mobile base is unconnected to a bottom wall of the tower assembly is movable between a stowed configuration proximate the tower assembly and a deployed configuration positioned away from the tower assembly and includes a grip member coupled to the leading edge of the panel. The partition apparatus includes a guide assembly having an upper guide member complementary to the upper fastener and operable for engaging the upper fastener, the upper guide member including a plurality of spacer segments each having a metallic core and being operable to maintain an angled configuration.

20 Claims, 18 Drawing Sheets

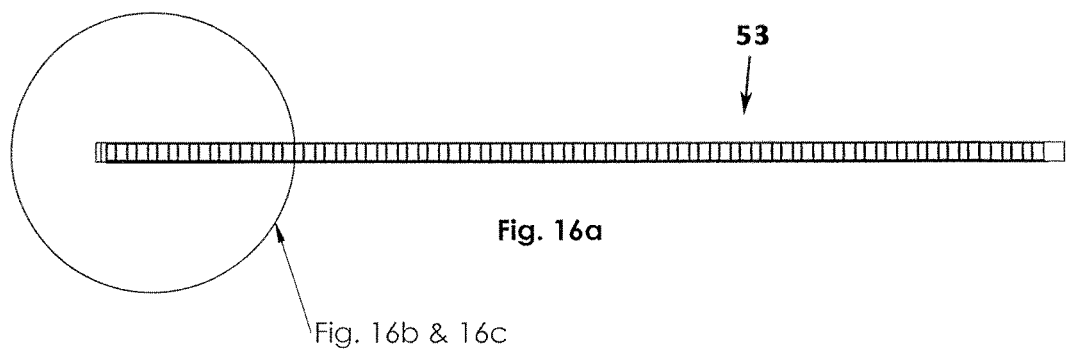
Fig. 16a
Fig. 16b & 16c
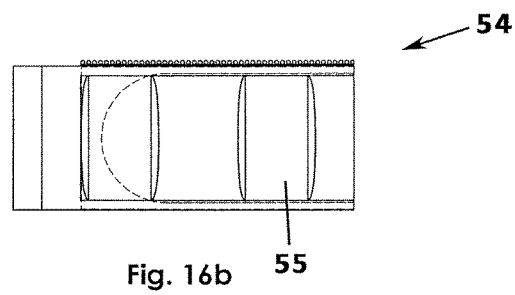
Fig. 16b
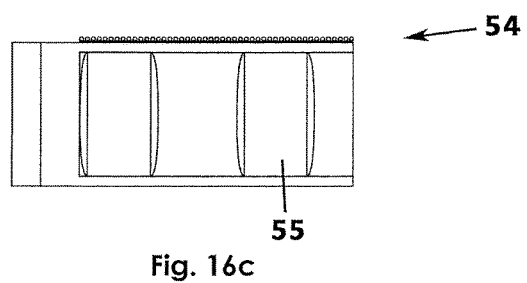
Fig. 16c

SELF-CLEANING RETRACTABLE PARTITION APPARATUS

BACKGROUND OF THE INVENTION

This invention relates generally to hospital patient area partition systems and, more particularly, to a self-cleaning retractable partition apparatus that disinfects a partition with ultraviolet light exposure as the partition is coiled into or uncoiled from a tower assembly.

Improving the experience of a patient in a hospital environment is of great concern to both hospital administrators and patients and their families. Whether suffering from an acute medical condition requiring only a short stay or a chronic condition or disease resulting in a longer stay, a patient values his privacy from nearby patients and benefits from any reduction in anxiety and stress. Since there is a limit to what a patient can bring to his room during a medical stay in order to promote his experience, it is largely up to the hospital administrators to provide excellent care and comfortable conditions.

One problem that hospitals and patients are mutually concerned about is the prevention of infections and spread of bacteria resulting from unsanitary conditions in a patient room. Specifically, the surface of privacy curtains, walls, or other privacy dividers is a common problem and one that is difficult to solve completely—even if the partition is wiped down regularly with a disinfectant wipe or towel.

Therefore, it would be desirable to have a partition apparatus for surrounding or defining a private area for a patient that is self-cleaning—meaning that the partition panel is cleaned automatically every time the partition is extended from or retracted onto a reel member. Further, it would be desirable to have a partition apparatus in which a flexible panel is uncoiled for use, may be extended in multiple directions as needed and which retracts easily to a stowed configuration. In addition, it would be desirable to have a partition apparatus that is portable and movable for storage or use in selected environments.

SUMMARY OF THE INVENTION

A self-cleaning retractable partition apparatus according to the present invention includes a tower assembly having a bottom wall and a top wall opposite the bottom wall and a plurality of side walls extending between the bottom and top walls that, together, define an interior area, the plurality of side walls including a front wall defining a slot allowing access to the interior area. The partition apparatus includes a primary ultraviolet light mounted to one of the bottom wall or the top wall operable to illuminate the interior area when energized. A partition assembly has a reel member extending upwardly from the bottom wall of the tower assembly and a panel having an inner edge coupled to the reel member and a leading edge opposite the inner edge, the panel having a flexible construction movable between a coiled configuration wrapped about the reel member and an uncoiled configuration extending away from the reel member. The panel includes a top edge extending between the inner edge and the leading edge, respectively, the top edge having an upper fastener extending along an entire extent of the top edge. A mobile base unconnected to the bottom wall of the tower assembly is movable between a stowed configuration proximate the tower assembly and a deployed configuration positioned away from the tower assembly and having a grip member extending upwardly from the mobile base and coupled to the leading edge of the panel.

The partition apparatus includes a guide assembly that includes an upper guide member having a configuration complementary to the upper fastener and operable for selectively engaging the upper fastener, the upper guide member including a plurality of spacer segments each having a metallic core and being operable to maintain an angled configuration.

Therefore, a general object of this invention is to provide a self-cleaning retractable partition apparatus in which a flexible panel may be coiled inside a tower assembly or extended and pulled away from the tower assembly so as to partition an area, such as in a hospital room.

Another object of this invention is to provide a self-cleaning retractable partition apparatus, as aforesaid, in which the flexible panel is disinfected by ultraviolet light when inside the tower assembly.

Still another object of this invention is to provide a self-cleaning retractable partition apparatus, as aforesaid, in which the flexible panel may be pulled out of the tower and positioned in one or more angled configurations.

Yet another object of this invention is to provide a self-cleaning retractable partition apparatus, as aforesaid, having a mobile base coupled to a leading edge of the panel and which may be pulled out and away from the tower assembly.

A further object of this invention is to provide a self-cleaning retractable partition apparatus, as aforesaid, that provides privacy and comfort to patients in a hospital environment.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 15a is a perspective view of the self-cleaning portable partition apparatus of FIG. 14;

FIG. 15b is an isolated view on an enlarged scale taken from FIG. 15a;

FIG. 16a is an isolated side view of a guide rail removed from the self-cleaning portable partition apparatus as in FIG. 1;

FIG. 16b is an isolated view on an enlarged scale taken from FIG. 16a;

FIG. 16c is another isolated view on an enlarged scale taken from FIG. 16a;

FIG. 17b is a sectional view taken along line 17b-17b of FIG. 17a;

FIG. 19b is an isolated view on an enlarged basis taken from a portion of FIG. 19a.

DESCRIPTION OF THE PREFERRED EMBODIMENT

Figure 1:
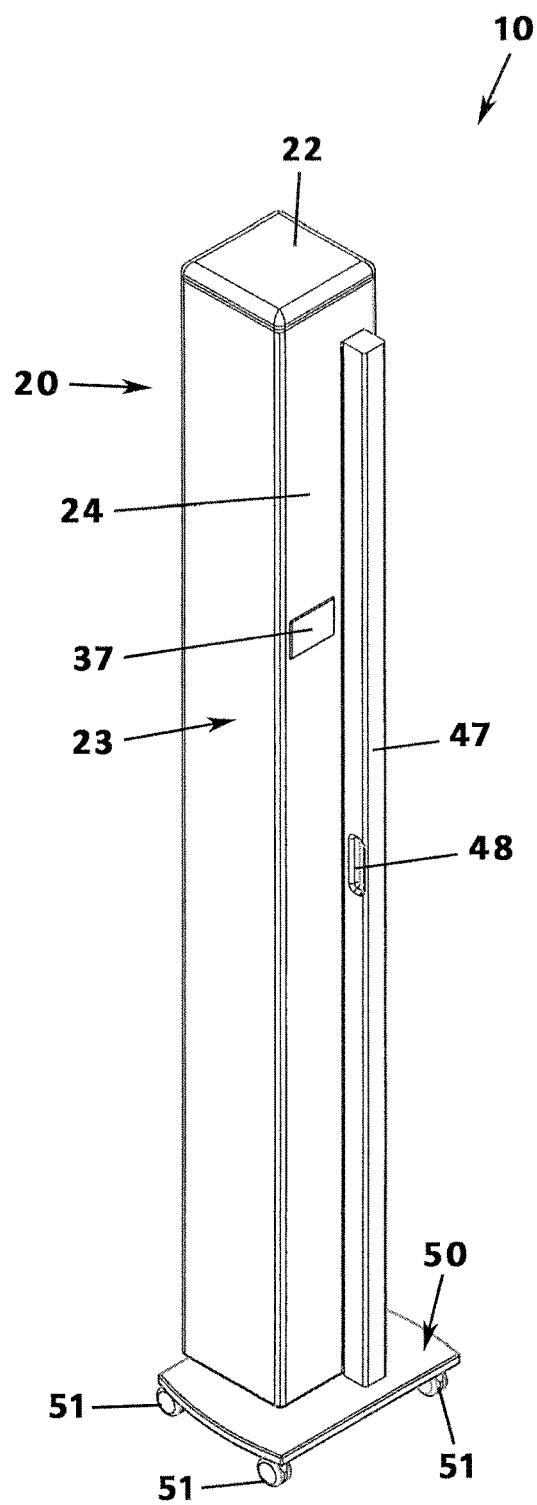
FIG. 1 is a perspective view of a self-cleaning portable partition apparatus according to a preferred embodiment of the present invention, illustrated in a fully retracted configuration.
Figure 2:
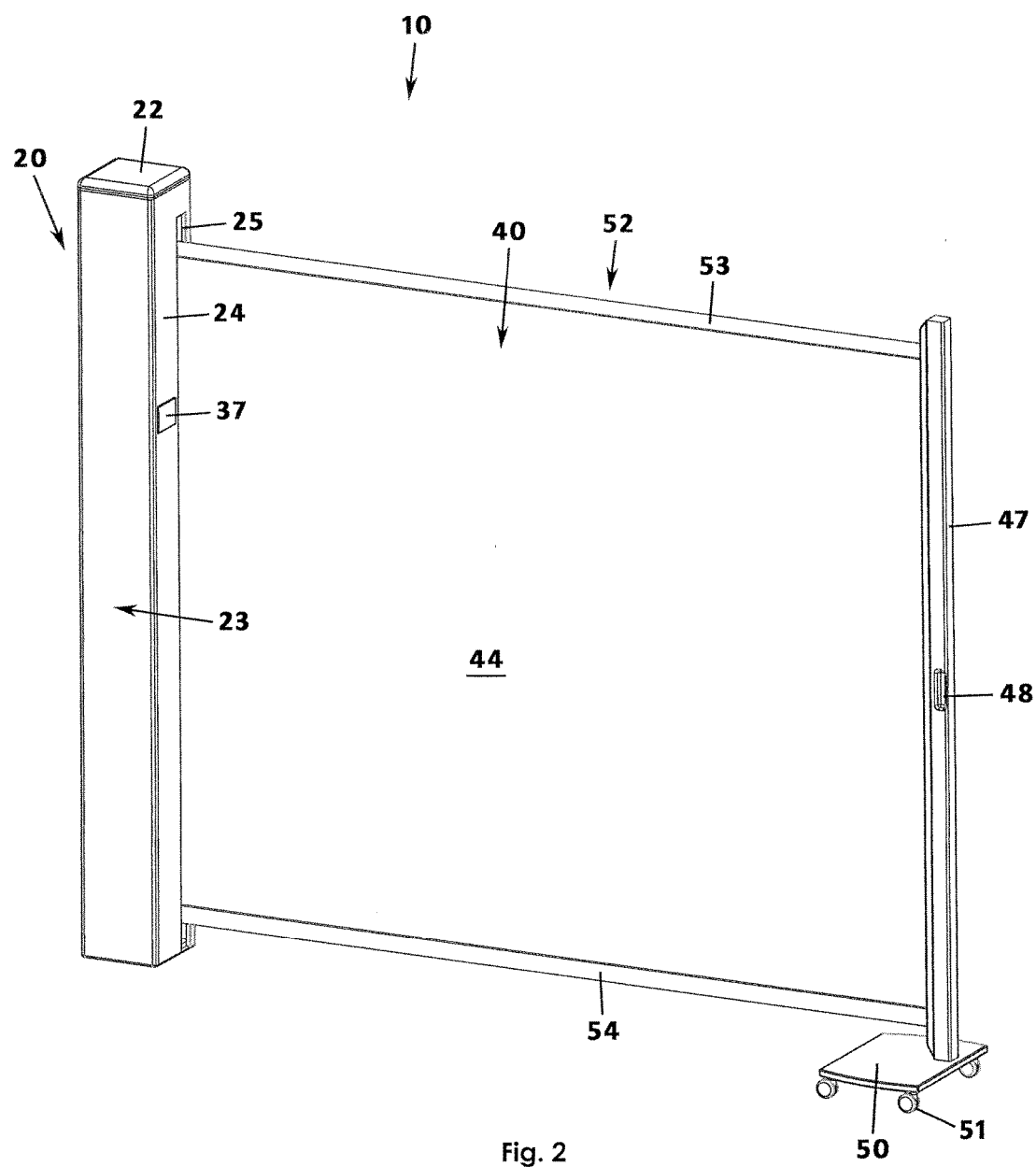
FIG. 2 is another perspective view of the self-cleaning portable partition apparatus as in FIG. 1, illustrated in a fully extended configuration.
Figure 3:
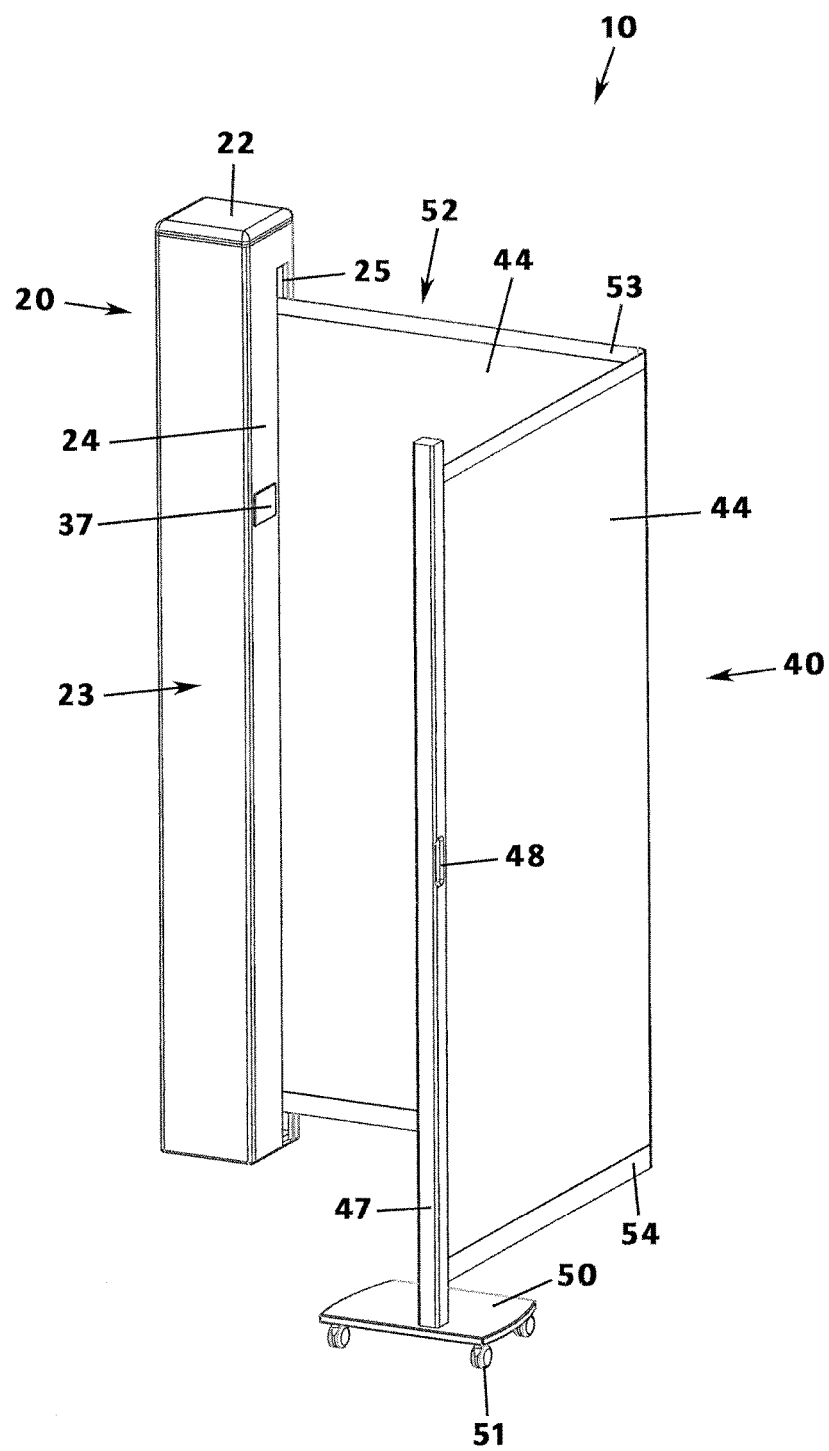
FIG. 3 is another perspective view of the self-cleaning portable partition apparatus as in FIG. 1, illustrated arranged in more than one direction.

A self-cleaning retractable partition apparatus according to a preferred embodiment of the present invention will now be described with reference to FIGS. 1 to 20 of the accompanying drawings. The self-cleaning retractable partition apparatus 10 includes a tower assembly 20, a partition assembly 40, a mobile base 50, and at least a primary ultraviolet light 30, and preferably a pair of auxiliary ultraviolet lights 32.

Figure 8:
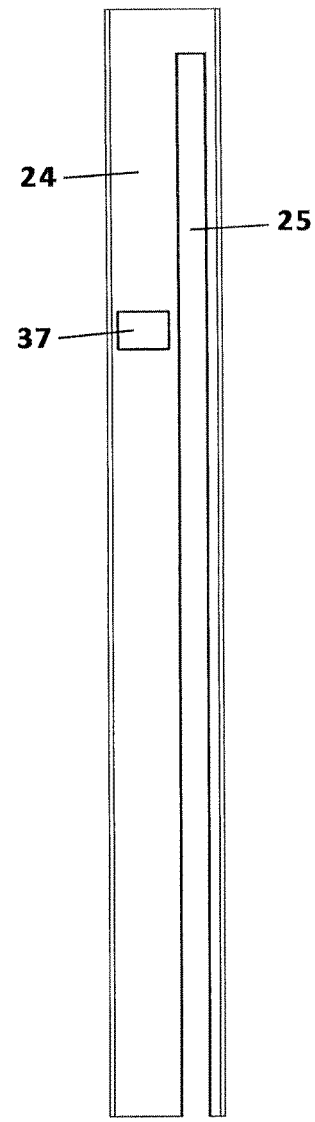
FIG. 8 is a front view illustrating a front wall removed from the tower assembly.
Figure 9:
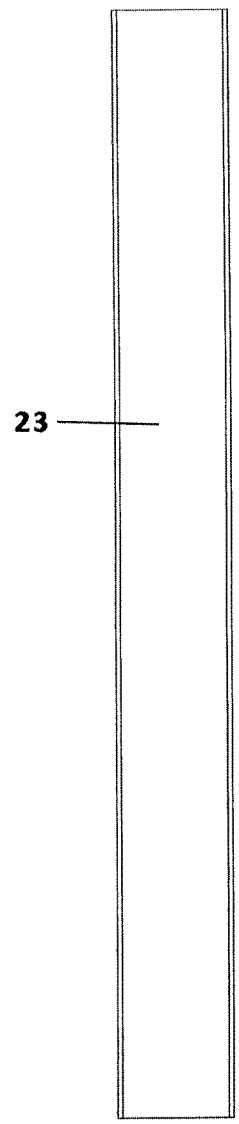
FIG. 9 is a front view illustrating a side wall removed from the tower assembly.
Figure 10:
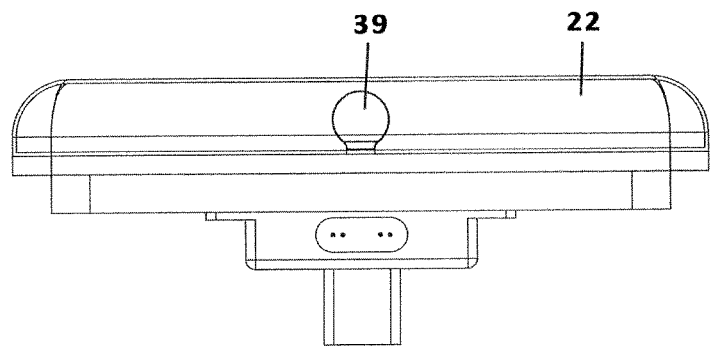
FIG. 10 is an isolated front view of the top wall of the tower assembly.
Figure 11:
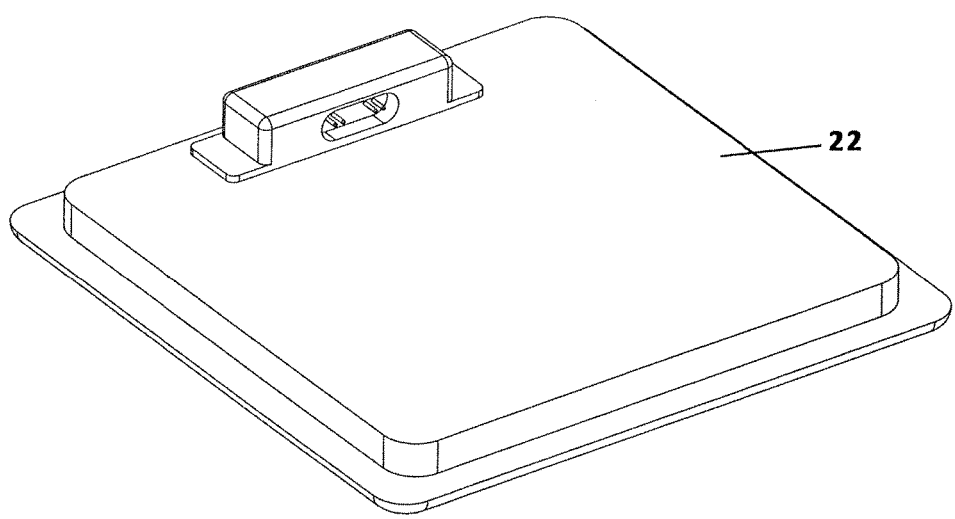
FIG. 11 is an isolated perspective view of the top wall of FIG. 10.
Figure 12:
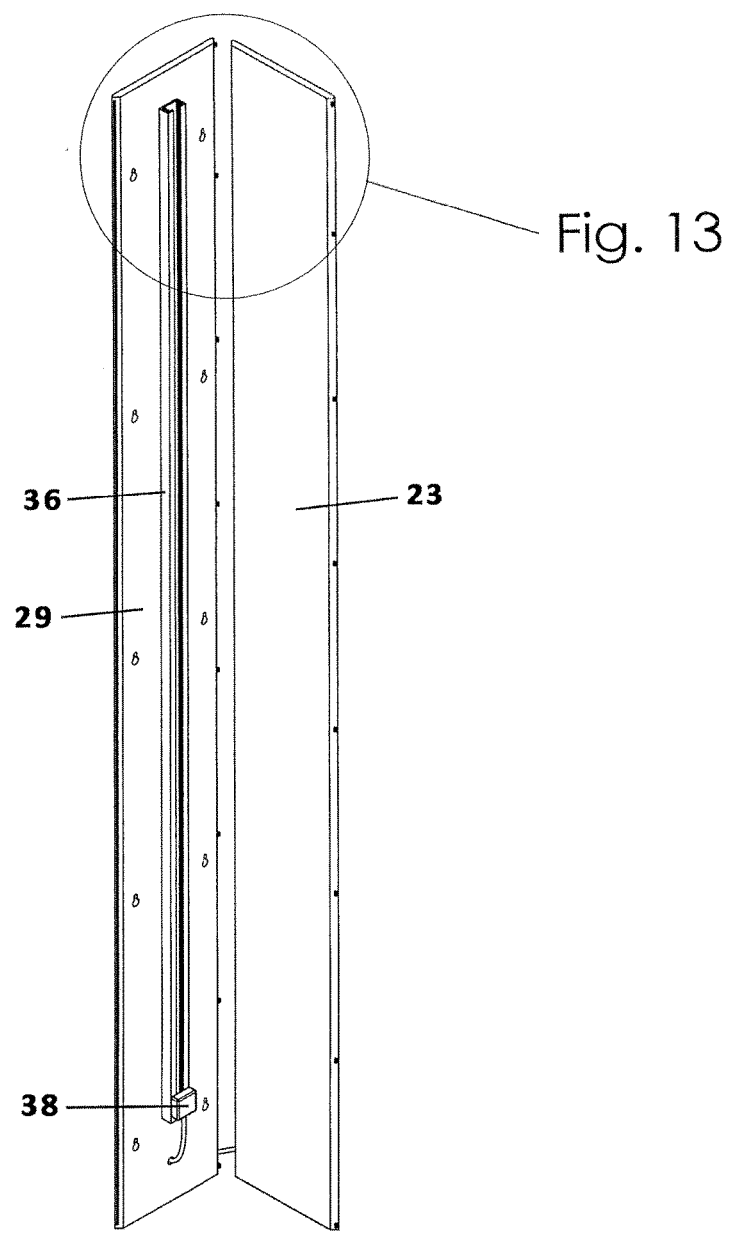
FIG. 12 is an exploded view of the tower assembly illustrating the assembly of selected walls thereof.
Figure 13:
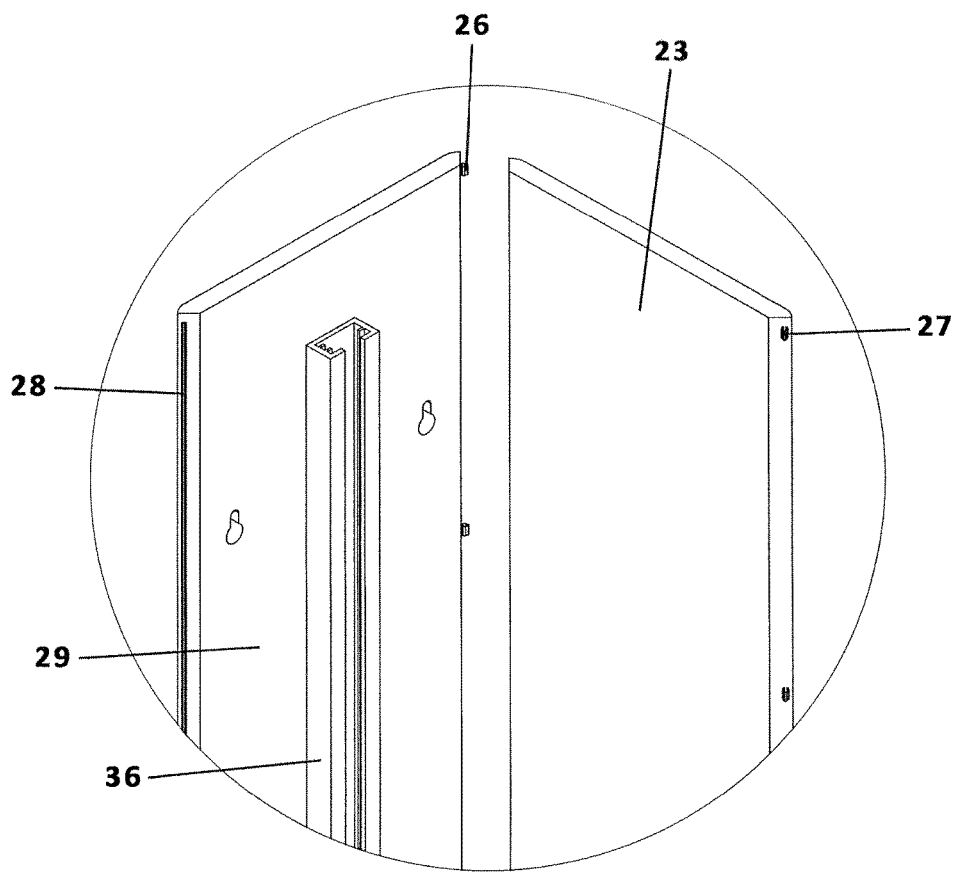
FIG. 13 is an isolated view on an enlarged scale taken from a portion of FIG. 12.
Figure 14:
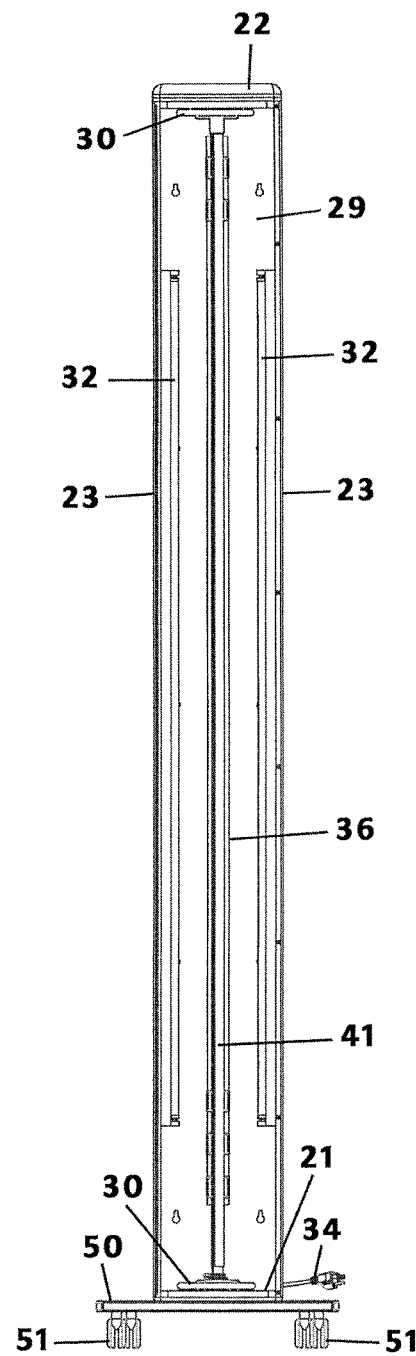
FIG. 14 is a front view of the self-cleaning portable partition apparatus as in FIG. 1 with the front panel and partition panel removed for clarity.

The tower assembly 20 provides a housing having a bottom wall 21, a top wall 22 that is parallel to and opposed to the bottom wall 21, and a plurality of side walls 23 extending between the bottom wall 21 and top wall 22. Together, the walls form the housing such that the tower assembly 20 defines an interior area. It is understood, that the tower assembly 20 may have a form other than a rectangular shape shown in the drawings. One of the plurality of side walls will be referred to as a front wall 24 which defines a slot 25 or open channel that allows access to or from the interior area of the tower assembly 20. The slot 25 is proximate the top wall 22 although displaced therefrom. The slot 25 has a linear configuration. The slot 25 is, therefore, closed at it upper whereas the slot 25 is open at its lower (FIG. 8). The slot 25 has a width that is sufficient to receive the panel 44 into our out of the interior area of the tower assembly 20 during deployment or retraction as will be described later. As shown in FIGS. 12 and 13 of the drawings, the plurality of side walls 23 may have respective pins 26, holes 27, and slits 28 so as to be coupled together in a manner that allows them also to be released, portable, and stored away when not in use or transported.

Preferably, the tower assembly 20 is secured to a wall structure 12 of a hospital room or other structure where use of a partition for privacy is desired. More particularly, one of the plurality of side walls 23 will be referred to as a back wall 29 and includes apertures or holes for receiving fasteners suitable to mount the entire tower assembly 20 to a wall structure 12 (FIG. 12). Preferably, the tower assembly 20 is mounted to a wall at a position in which the bottom wall 21 is displaced a few inches above a floor surface 14 so that the mobile base 50 may be slidably positioned beneath the bottom wall 21 at a stowed configuration (FIG. 6) as will be described later.

With further reference to the tower assembly 20, a primary ultraviolet light ("UV-C light") 30 may be mounted to an undersurface (i.e. a lower or interior surface) of the top wall 22. Another primary ultraviolet light 30 may be mounted atop an upper surface (i.e. an interior surface) of the bottom wall 21. Ultraviolet light or UV light is classified in terms of their wavelength and as being UVA, UVB, or UVC light rays. A UV-C light is unlikely to damage a person's skin but is effective to disinfect against bacteria growing on an object. In the present instance, each primary UV light 30 may be a UV-C light. Also, the primary UV light 30 may be a pair of primary UV lights. Preferably, each primary UV light 30 is a UV-C light in which the "C" refers to a preferred wavelength of UV light and which is specifically configured and operable to disinfect and kill bacteria.

In addition, auxiliary ultraviolet light 32 may be mounted to an interior surface of a side wall of the tower assembly 20 and be directed to illuminate the interior space. Preferably, the auxiliary ultraviolet light 32 includes a pair of ultraviolet lights positioned on inner surfaces of a pair of opposed side walls and directed to expose the large flat portions of the panel 44 to UV light.

Each of the ultraviolet lights described above is preferably electrically connected to an electrical power source, such as to a 110-volt electrical outlet via an electrical cord 34. The electrical cord may be hidden and protected in a three-wire track rail 36 or the like and may include appropriate power adapters 38 (FIGS. 7A and 15B, respectively) to properly regulate voltage received from the power source. Although not preferred, it is contemplated that the electrical current needed for the UV lights could be supplied from batteries and, preferably, rechargeable batteries.

Still further, the tower assembly 20 may include a control module 37, such as a touch-screen input screen, positioned on an exterior surface of the front wall 24 and is configured and operable to display input options and receive input instructions from a user. The control module 37 is electrically connected to the ultraviolet lights discussed above and is operable to energize respective lights when instructed or programmed to do so. A light emitting diode 39 may be positioned on the top wall 22 or other wall and is electrically connected to the ultraviolet lights and is operable to indicate when the lights are operable.

In another aspect, the self-cleaning retractable partition apparatus 10 includes a partition assembly 40 having a reel member 41 and a panel 44 coiled around and extendable away from the reel member 41. More particularly, the reel member 41 may be a rod having a cylindrical configuration that extends upwardly from the bottom wall 21 of the tower assembly 20. It is understood the reel member 41 may be mounted in an axial arrangement extending substantially between the bottom wall 21 and top wall 22 and is rotatable to coil the panel 44 about the rod and as the panel 44 is extended as will be described below. The panel 44 that acts as the partition includes an inner edge 45 that is coupled to the reel member 41 and a leading edge 46 opposite the inner edge 45. The panel 44 may be constructed of a generally flexible material so that it may be coiled and uncoiled about the reel member 41. The flat sides of the panel 44 may include indicia such as colors, symbols, imprinted messages, corporate or sponsorship messages, or artwork so as to enhance a patient's experience in a hospital environment.

The leading edge 46 is coupled to an upstanding grip member 47, the grip member 47 being used to pull the panel 44 from the coiled configuration to the uncoiled configuration. The grip member 47 may include a handle 48 configured to receive a finger or fingers of a user and to enhance a user's ability to pull the grip member 47 and, thus, the panel 44 away from the tower assembly 20.

In a related aspect, the panel 44 may include spacer flanges (not shown) configured to maintain space between rolls of the panel 44 when it is coiled about the rod of the reel member 41, it being understood that the UV light rays are more effective if they are given more opportunity to impact the surfaces of the panel 44 in the coiled configuration.

Figures 15A, 15B:
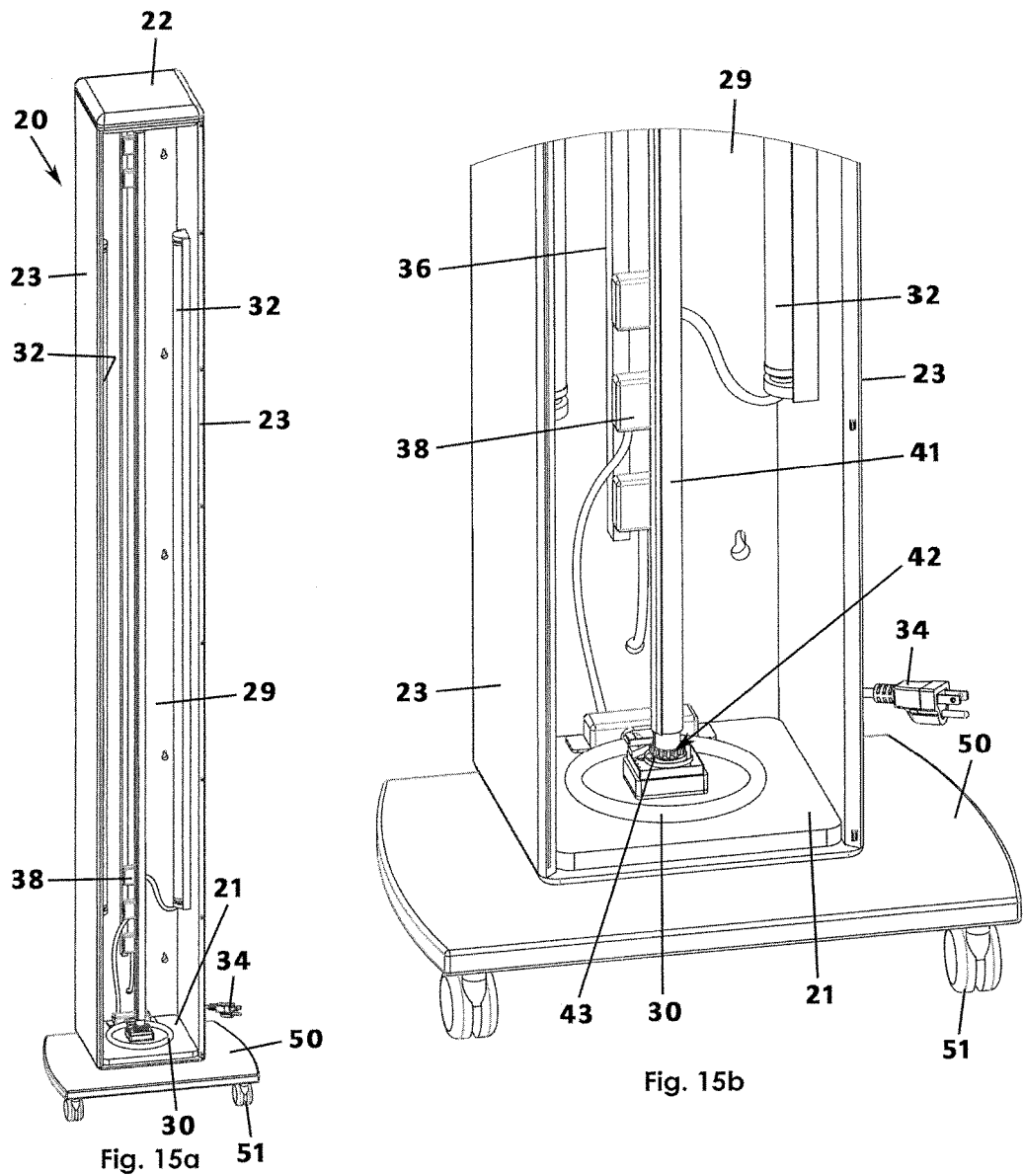
Figure 17A:
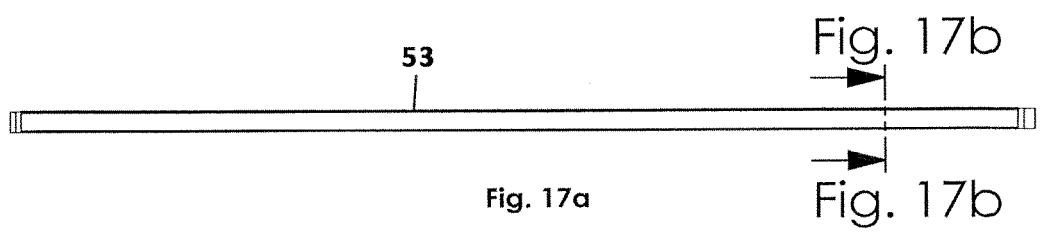
FIG. 17a is a back view of a guide rail removed from the self-cleaning portable partition apparatus as in FIG. 1.
Figure 17B:
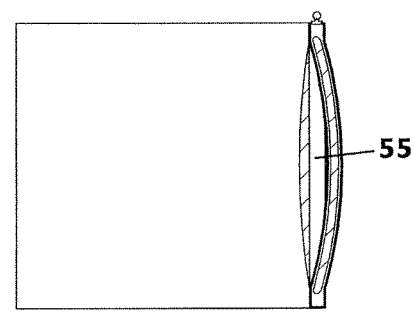
Figure 18:
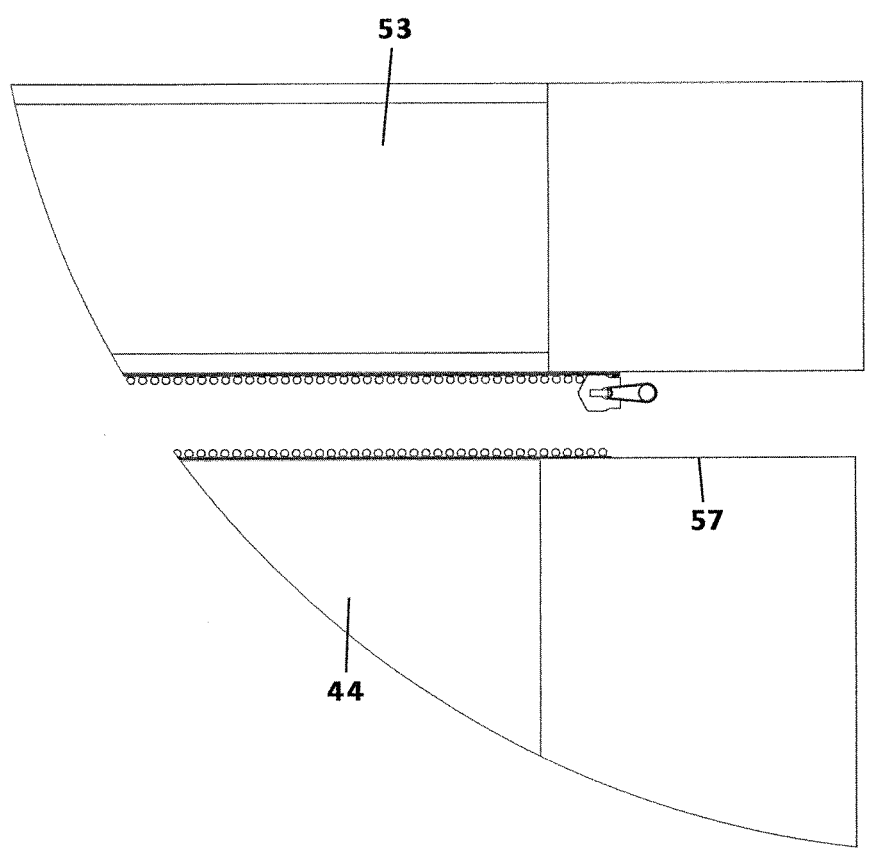
FIG. 18 is an isolated exploded view of a guide rail ready for engagement with a top edge of the partition panel of FIG. 1.

To regulate the coiling or uncoiling of the panel 44, the reel member 41 may include a ratchet-pawl spring assembly 42 positioned at a bottom or base of the reel member 41 (FIG. 15b). The specific construction of a ratchet-pawl spring assembly 42 is known in the art and will not be described in detail. However, it is understood that a ratchet gear 43 is rotated by the rotation of the rod in a stepwise manner and according to the size of the gear teeth. As the ratchet gear 43 is rotated, it is held in a rotated configuration by the pawl repeatedly dropping into a slot between the gear teeth. In other words, the pawl keeps the ratchet gear from rotating when the pulling pressure is stopped. But, then, the spring is operable to cause the panel to retract and coil around the rod of the reel member 41, such as when actuated by a sharp tug on the panel 44 (in the nature of tugging a spring-loaded blind).

Figure 4:
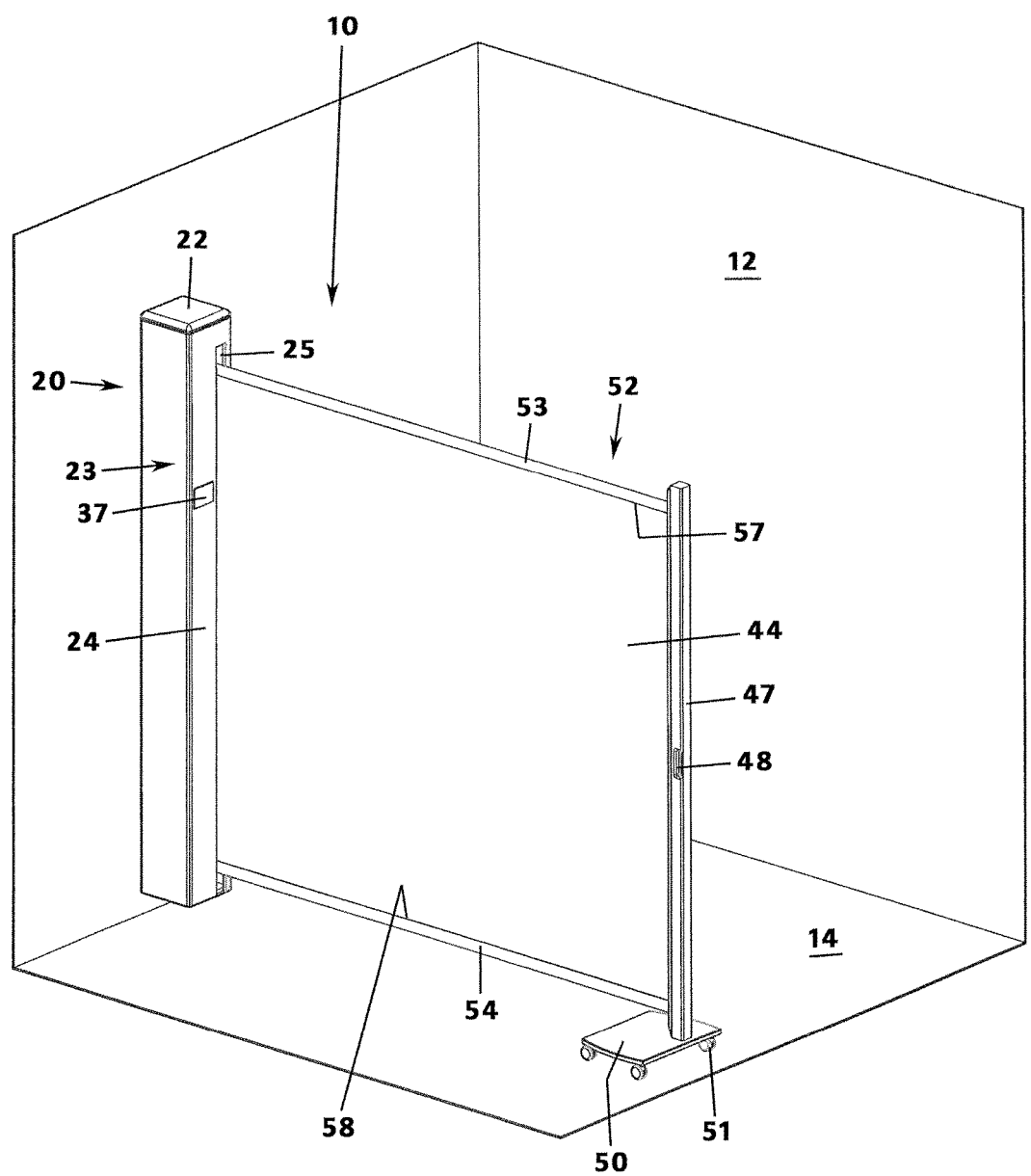
FIG. 4 is a perspective view of the self-cleaning portable partition apparatus as in FIG. 2, illustrated in use in a room environment.
Figure 5:
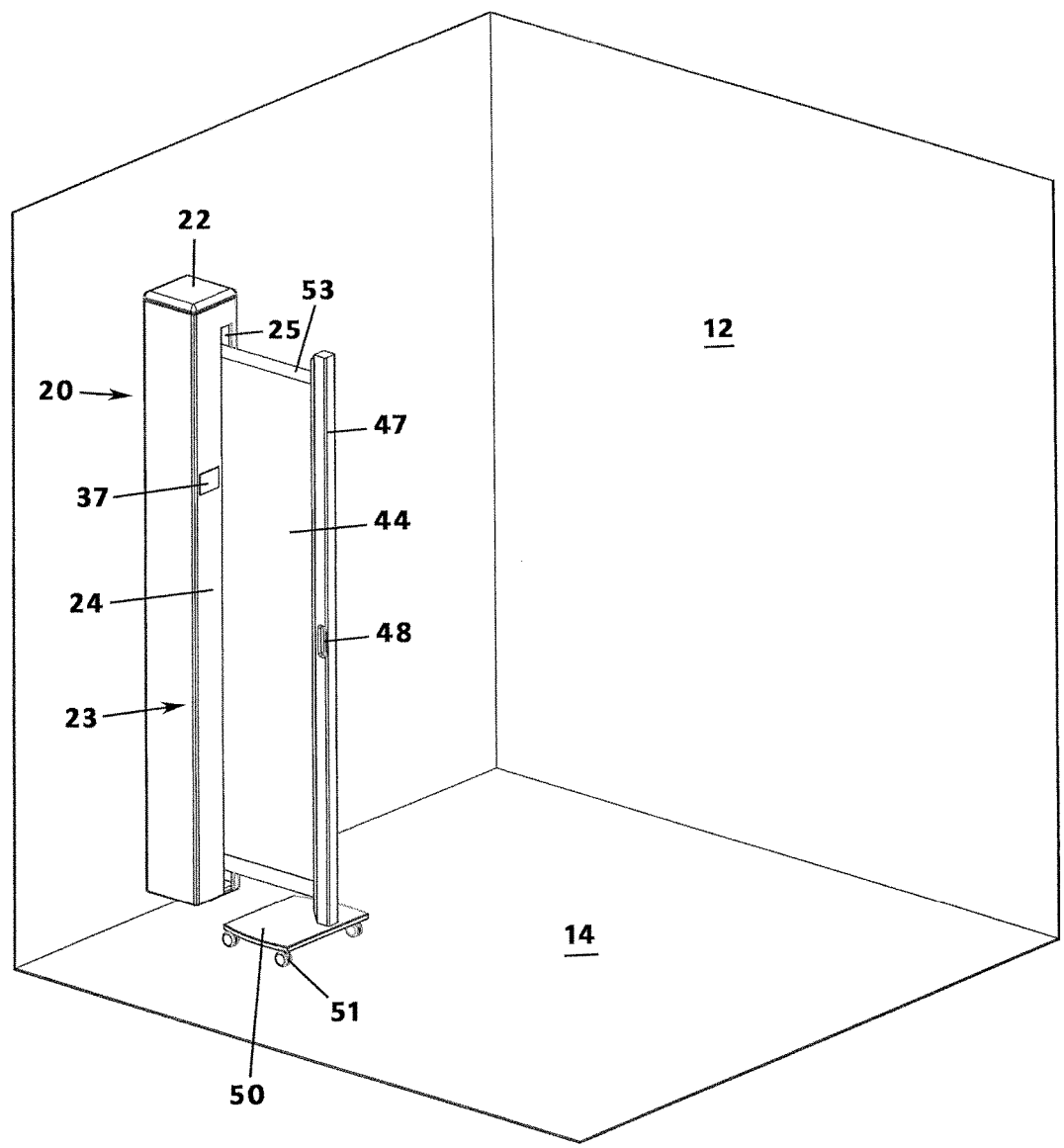
FIG. 5 is a perspective view of the self-cleaning portable partition apparatus as in FIG. 1, illustrated in a partially extended configuration and in use in a room environment.
Figure 6:
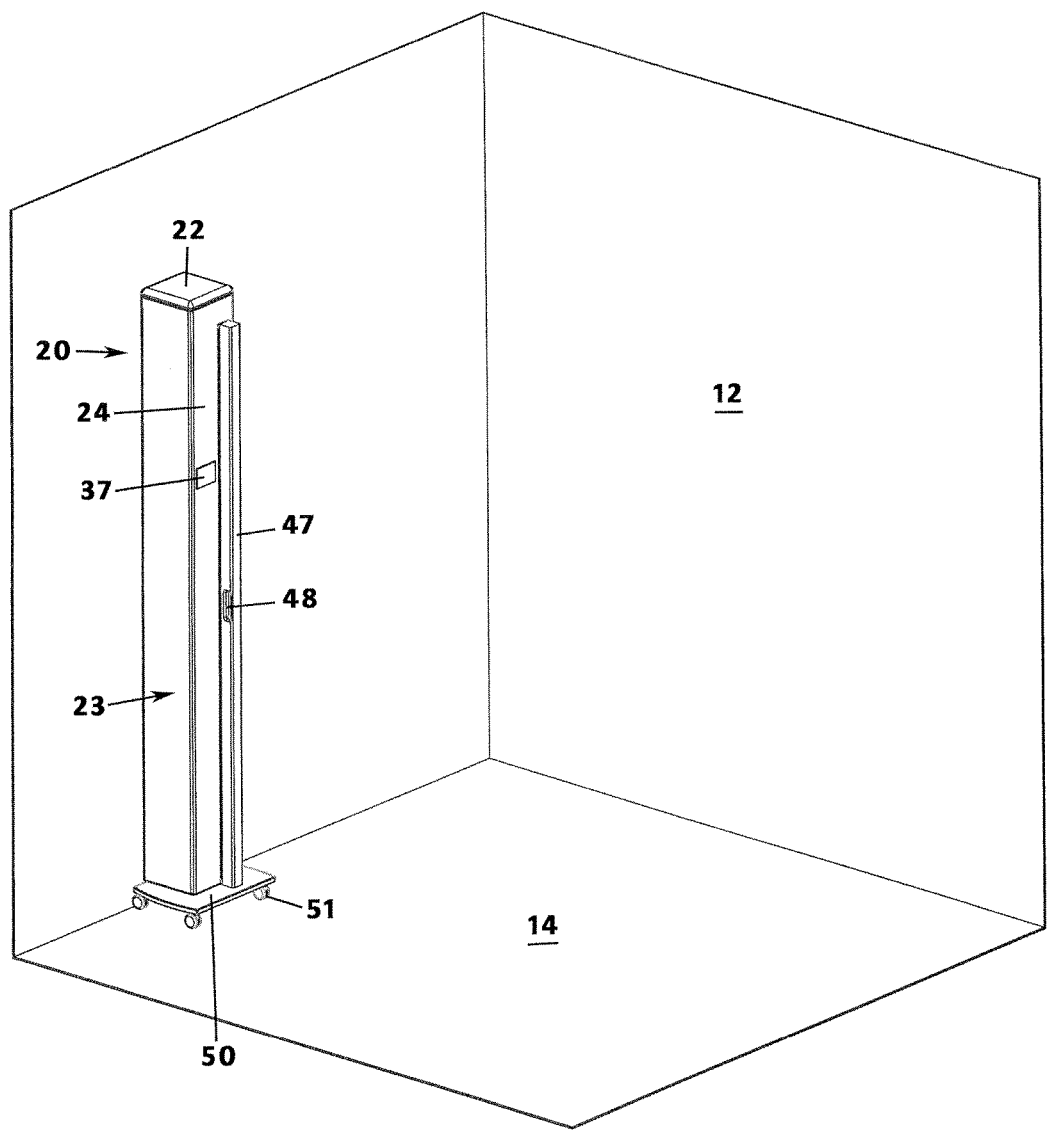
FIG. 6 is a perspective view of the self-cleaning portable partition apparatus as in FIG. 1, illustrated in use in a room environment.
Figure 7:
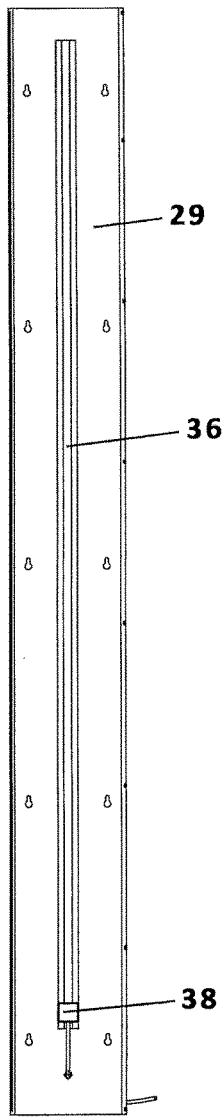
FIG. 7 is a front view illustrating a back wall removed from the tower assembly.

In a related aspect, the self-cleaning retractable partition apparatus 10 includes a mobile base 50 that includes a planar portion having a plurality of wheels 51 such that the mobile base 50 is movable between a stowed configuration proximate the tower assembly 20 (FIG. 6) and a deployed configuration displaced and positioned away from the tower assembly 20 (FIGS. 4 and 5). It is noted that the grip member 47 is coupled to an upper surface of the planar portion of the mobile base 50 and, accordingly, the mobile base 50 is operably coupled to the tower assembly 20. It can be seen in the figures that at the stowed configuration, the mobile base 50 is received under and adjacent to the bottom wall 21 of the tower assembly 20 (FIG. 6) and increasingly displaced from the tower assembly 20 as the mobile base 50 is deployed and the panel 44 is uncoiled (FIGS. 5 and 4).

With further reference to the panel 44, the panel 44 may include a top edge 57 opposite a bottom edge 58 each extending substantially between the inner edge 45 and leading edge 46. The top edge 57 and bottom edge 58 may be configured as an elongate fastener such as a half of a zipper, the operation of which will become apparent as described below.

In still another aspect, the self-cleaning retractable partition apparatus 10 includes a guide assembly 52 operable to give stability, strength, and form to the panel 44, i.e. to enable the panel 44 to stay in a desired position, to be bent or angled, and to give the appearance of being a firm panel. More particularly, the guide assembly 52 includes an upper guide member 53 that has a configuration that is complementary to the upper fastener of the top edge 57 of the panel—in other words, in the form of a zipper, and operable to engage the zipper of the top edge 57. Similarly the guide assembly 52 includes an lower guide member 54 that has a configuration that is complementary to the lower fastener of the bottom edge 58 of the panel—in other words in the form of a zipper, and operable to engage the zipper of the bottom edge.

Figure 19A:
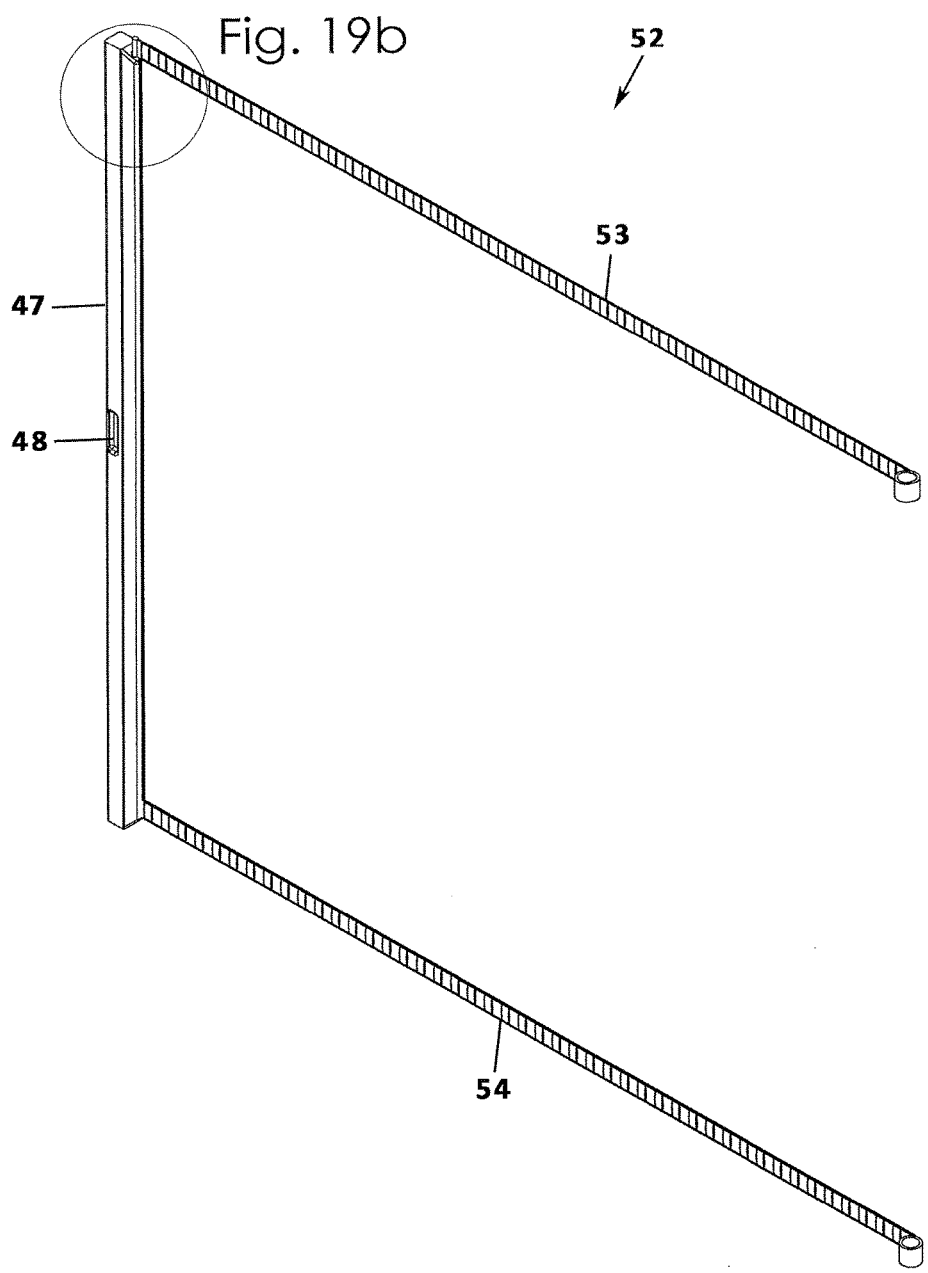
FIG. 19a is a perspective view of an upper guide member and a lower guide member coupled to an upstanding grip member with the partition panel removed for clarity.
Figure 19B:
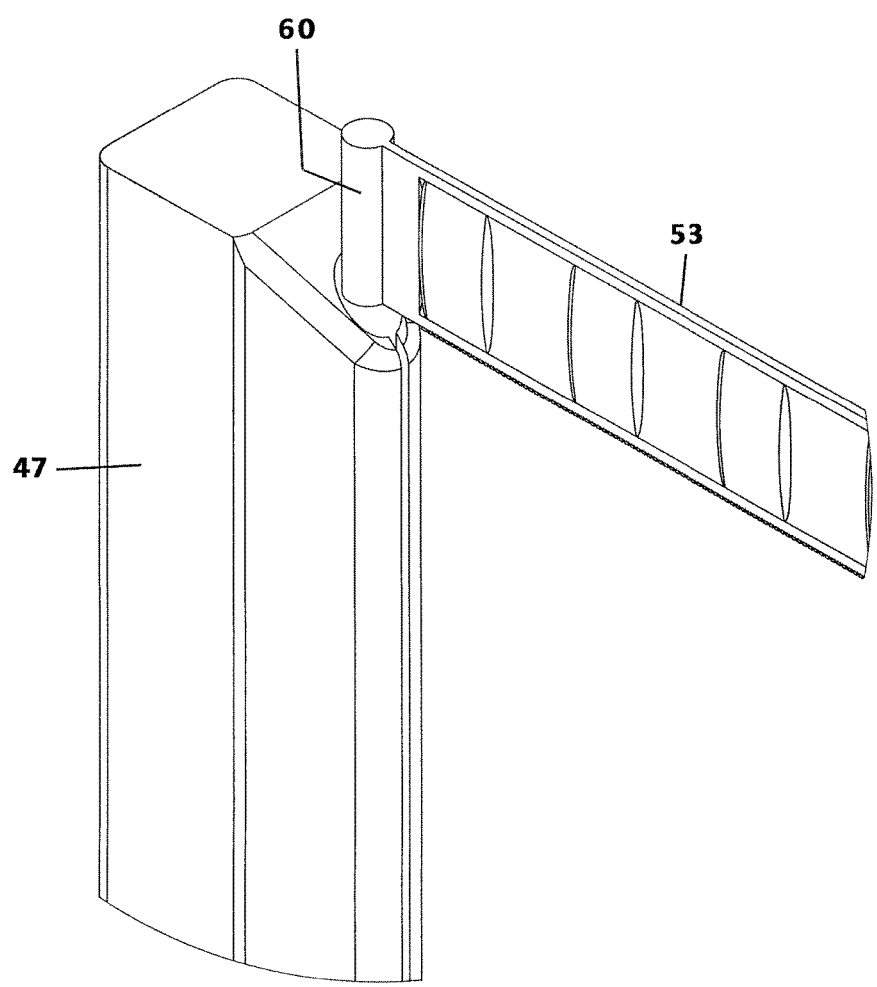
Figure 20:
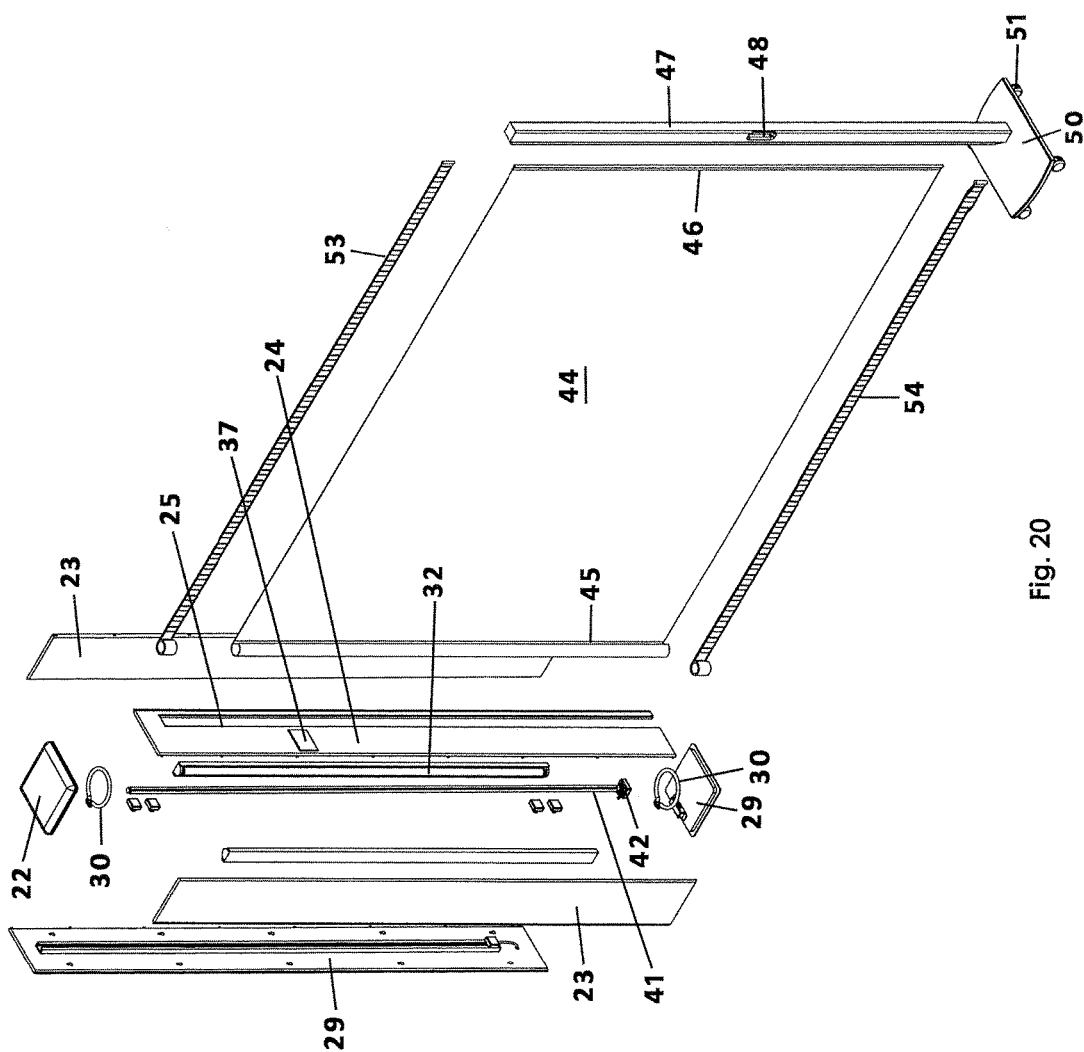
FIG. 20 is an exploded view of the self-cleaning portable partition apparatus as in FIG. 1.

Even more specifically, the upper guide member 53 includes a plurality of spacer segments 55, each spacer segment 55 having a metallic core—such as made of spring steel—that is capable of being bent or angled and then holding the bent configuration until straightened by manual manipulation. Similarly, a lower guide member 54 has a similar or same construction and operation. Each guide member includes a first end having a first guide rail 60 configured to be received into a complementary channel defined by the grip member 47 (FIG. 19b). At an opposite end, however, the guide members, like the inner edge of the panel 44 are wrapped about and coupled to or captured by the reel member 41.

In use, the ultraviolet lights may be energized automatically when the panel is fully recoiled, is being uncoiled or recoiled, or at other times by manual input to the control module 37. The panel 44 may be uncoiled and extended by outward movement of the mobile base 50 via the wheels 51 thereof. The panel 44 may be extended outwardly from the tower assembly 20 in a linear path or with one or more bends as shown and described. In addition, the guide assembly 52 is fastened to the top or bottom of the panel 44 to provide strength, stability, and the directional functionality as described above.

It is understood that while certain forms of this invention have been illustrated and described, it is not limited thereto except insofar as such limitations are included in the following claims and allowable functional equivalents thereof.

The invention claimed is:

1. A self-cleaning retractable partition apparatus, comprising:
    a tower assembly having a bottom wall and a top wall opposite said bottom wall and a plurality of side walls extending between said bottom and top walls that, together, define an interior area, said plurality of side walls including a front wall defining a slot allowing access to said interior area;
    a primary ultraviolet light mounted to one of said bottom wall or said top wall operable to illuminate said interior area when energized;
    a partition assembly having a reel member extending upwardly from said bottom wall of said tower assembly and a panel having an inner edge coupled to said reel member and a leading edge opposite said inner edge, said panel having a flexible construction movable between a coiled configuration wrapped about said reel member and an uncoiled configuration extending away from said reel member;
    a mobile base unconnected to said bottom wall of said tower assembly and movable between a stowed configuration proximate said tower assembly and a deployed configuration positioned away from said tower assembly and having a grip member extending upwardly from said mobile base and coupled to said leading edge of said panel.

2. The self-cleaning retractable partition apparatus as in claim 1, wherein said front wall of said tower assembly defines a slot having an upper end proximate said top wall that is closed and a lower end opposite said upper end that is open, said slot having a width operable for receiving panel into said interior area of said tower assembly.

3. The self-cleaning retractable partition apparatus as in claim 1, wherein:
said plurality of side walls of said tower assembly includes a back wall opposite said front wall that is operable for suspending said tower assembly above a floor surface such that said bottom wall is displaced from said floor surface;
said base assembly is positioned immediately beneath said bottom wall of said tower assembly when in said stowed configuration.

4. The self-cleaning retractable partition apparatus as in claim 1, wherein said primary ultraviolet light includes a pair of primary ultraviolet lights coupled to a bottom side of said top wall and a top side of said bottom wall, respectively, said pair of primary ultraviolet lights being directed to illuminate said interior area when energized.

5. The self-cleaning retractable partition apparatus as in claim 4, further comprising a pair of auxiliary ultraviolet lights coupled to a pair of interior surfaces of a pair of said plurality of side walls, respectively, and operably directed to illuminate said interior area when energized.

6. The self-cleaning retractable partition apparatus as in claim 5, wherein said primary ultraviolet light and said pair of auxiliary ultraviolet lights is electrically connected to an electrical power source.

7. The self-cleaning retractable partition apparatus as in claim 1, wherein said mobile base includes a plurality of wheels operable for moving said mobile base from said stowed configuration to said deployed configuration.

8. The self-cleaning retractable partition apparatus as in claim 1, wherein said grip member of said mobile base includes a handle operable for a user to grasp and pull said base member toward said deployed configuration.

9. The self-cleaning retractable partition apparatus as in claim 1, further comprising a control module positioned on an exterior surface of said front wall of said tower assembly, said control module electrically connected to said primary ultraviolet light and operable to receive input commands from a user and to energize said primary ultraviolet light.

10. The self-cleaning retractable partition apparatus as in claim 1, wherein:
said reel member includes a rod having a cylindrical configuration and is mounted in an axial arrangement extending between said bottom wall and said top wall of said tower assembly;
said reel member includes a ratchet-pawl spring assembly having a ratchet gear that is rotated stepwise when said partition assembly is moved toward said deployed configuration and a pawl maintains said rotation, respectively, and having a spring operable to return said mobile base assembly to said stowed configuration when said pawl is released from said ratchet gear.

11. The self-cleaning retractable partition apparatus as in claim 1, wherein said panel includes a top edge extending between said inner edge and said leading edge, respectively, said top edge having an upper fastener extending along an entire extent of said top edge, said self-cleaning retractable partition apparatus further comprising:
a guide assembly that includes an upper guide member having a configuration complementary to said upper fastener and operable for selectively engaging said upper fastener;
wherein said upper guide member includes a plurality of spacer segments each having a metallic core and operable to maintain an angled configuration.

12. The self-cleaning retractable partition apparatus as in claim 11, wherein:

said upper guide member includes a first end having a first guide rail releasably coupled to said grip member of said tower assembly.

13. A self-cleaning retractable partition apparatus, comprising:
a tower assembly having a bottom wall and a top wall opposite said bottom wall and a plurality of side walls extending between said bottom and top walls that, together, define an interior area, said plurality of side walls including a front wall defining a slot having an upper end proximate said top wall that is closed and a lower end opposite said upper end that is open, said slot having a width operable for receiving panel into said interior area of said tower assembly;
a primary ultraviolet light mounted to one of said bottom wall or said top wall operable to illuminate said interior area when energized;
a partition assembly having a reel member extending upwardly from said bottom wall of said tower assembly and a panel having an inner edge coupled to said reel member and a leading edge opposite said inner edge, said panel having a flexible construction movable between a coiled configuration wrapped about said reel member and an uncoiled configuration extending away from said reel member;
wherein said panel includes a top edge extending between said inner edge and said leading edge, respectively, said top edge having an upper fastener extending along an entire extent of said top edge;
a mobile base unconnected to said bottom wall of said tower assembly and movable between a stowed configuration proximate said tower assembly and a deployed configuration positioned away from said tower assembly and having a grip member extending upwardly from said mobile base and coupled to said leading edge of said panel;
a guide assembly that includes an upper guide member having a configuration complementary to said upper fastener and operable for selectively engaging said upper fastener;
wherein said upper guide member includes a plurality of spacer segments each having a metallic core and being operable to maintain an angled configuration;
wherein said upper guide member includes a first end having a first guide rail releasably coupled to said grip member of said tower assembly.

14. The self-cleaning retractable partition apparatus as in claim 13, wherein:
said plurality of side walls of said tower assembly includes a back wall opposite said front wall that is operable for suspending said tower assembly above a floor surface such that said bottom wall is displaced from said floor surface;
said base assembly is positioned immediately beneath said bottom wall of said tower assembly when in said stowed configuration.

15. The self-cleaning retractable partition apparatus as in claim 13, wherein said primary ultraviolet light includes a pair of primary ultraviolet lights coupled to a bottom side of said top wall and a top side of said bottom wall, respectively, said pair of primary ultraviolet lights being directed to illuminate said interior area when energized.

16. The self-cleaning retractable partition apparatus as in claim 15, further comprising a pair of auxiliary ultraviolet lights coupled to a pair of interior surfaces of a pair of said plurality of side walls, respectively, and operably directed to illuminate said interior area when energized.

17. The self-cleaning retractable partition apparatus as in claim 13, wherein said mobile base includes a plurality of wheels operable for moving said mobile base from said stowed configuration to said deployed configuration.

18. The self-cleaning retractable partition apparatus as in claim 13, wherein said grip member of said mobile base includes a handle operable for a user to grasp and pull said base member toward said deployed configuration.

19. The self-cleaning retractable partition apparatus as in claim 13, further comprising a control module positioned on an exterior surface of said front wall of said tower assembly, said control module being electrically connected to said primary ultraviolet light and operable to receive input commands from a user and to energize said primary ultraviolet light.

20. The self-cleaning retractable partition apparatus as in claim 13, wherein:
   said reel member includes a rod having a cylindrical configuration and is mounted in an axial arrangement extending between said bottom wall and said top wall of said tower assembly;
   said reel member includes a ratchet-pawl spring assembly having a ratchet gear that is rotated stepwise when said partition assembly is moved toward said deployed configuration and a pawl maintains said rotation, respectively, and having a spring operable to return said mobile base assembly to said stowed configuration when said pawl is released from said ratchet gear.

\* \* \* \* \*